(12) United States Patent
Ollivier et al.

(10) Patent No.: US 10,850,110 B2
(45) Date of Patent: Dec. 1, 2020

(54) IN SITU IMPLANTATION ACCESSORY FOR AN AUTONOMOUS INTRACARDIAC CAPSULE

(71) Applicant: SORIN CRM SAS, Clamart (FR)

(72) Inventors: Jean-François Ollivier, Gif sur Yvette (FR); Willy Régnier, Longjumeau (FR)

(73) Assignee: Sorin CRM SAS, Clamart (FR)

( * ) Notice: Subject to any disclaimer, the term of this patent is extended or adjusted under 35 U.S.C. 154(b) by 85 days.

(21) Appl. No.: 16/295,688

(22) Filed: Mar. 7, 2019

(65) Prior Publication Data

US 2019/0201685 A1    Jul. 4, 2019

Related U.S. Application Data

(62) Division of application No. 15/071,015, filed on Mar. 15, 2016, now Pat. No. 10,226,622.

(30) Foreign Application Priority Data

Mar. 16, 2015  (FR) ..................................... 15 52108

(51) Int. Cl.
    *A61B 18/12*    (2006.01)
    *A61N 1/375*    (2006.01)
    (Continued)

(52) U.S. Cl.
    CPC ..... *A61N 1/37518* (2017.08); *A61M 25/0082* (2013.01); *A61N 1/056* (2013.01);
    (Continued)

(58) Field of Classification Search
    USPC ........................................................ 607/122
    See application file for complete search history.

(56) References Cited

U.S. PATENT DOCUMENTS

| | | | |
|---|---|---|---|
| 2006/0089637 A1* | 4/2006 | Werneth ................. | A61B 18/18 606/41 |
| 2006/0106375 A1* | 5/2006 | Werneth ............. | A61B 18/1492 606/32 |

(Continued)

FOREIGN PATENT DOCUMENTS

| | | |
|---|---|---|
| EP | 2 394 695 A1 | 12/2011 |
| EP | 2 818 201 | 12/2014 |
| WO | WO-2012/082755 A1 | 6/2012 |

OTHER PUBLICATIONS

Preliminary Search Report for French Patent Application No. 1552108, dated Sep. 30, 2015, 2 pages.

*Primary Examiner* — Nicole F Lavert
(74) *Attorney, Agent, or Firm* — Foley & Lardner LLP

(57) ABSTRACT

This accessory comprises a remotely steerable catheter (40) extended by a tip (50) comprising a base (52) to which the catheter (40) connects to and a cylindrical portion (54) defining a volume (56) suitable for housing the capsule (10). A sub-catheter (30) and the capsule are telescopically extendable with respect to the catheter between i) a retracted position and a deployed position wherein the capsule is removed from the connector and is carried by the distal end of the sub-catheter, and the distal end of sub-catheter and the proximal region (18) of the capsule being provided with disconnectable means of attachment (20, 36). The tip presents, between its base (52) and its cylindrical portion (54), a flexible portion (58) providing, between the base and the cylindrical portion, an elastic deformability in bending and compression.

20 Claims, 2 Drawing Sheets

(51) Int. Cl.
  *A61N 1/372*   (2006.01)
  *A61M 25/00*   (2006.01)
  *A61N 1/05*    (2006.01)
  *A61N 1/362*   (2006.01)
  A61B 17/34    (2006.01)
  A61B 17/00    (2006.01)

(52) U.S. Cl.
  CPC ............. *A61N 1/057* (2013.01); *A61N 1/362* (2013.01); *A61N 1/372* (2013.01); *A61N 1/375* (2013.01); *A61N 1/3756* (2013.01); *A61N 1/37205* (2013.01); *A61B 17/3468* (2013.01); *A61B 2017/003* (2013.01); *A61N 1/0563* (2013.01); *A61N 2001/058* (2013.01)

(56) References Cited

U.S. PATENT DOCUMENTS

2007/0083194 A1*  4/2007  Kunis ................ A61B 18/1492
                                                    606/41
2009/0204170 A1   8/2009  Hastings et al.

\* cited by examiner

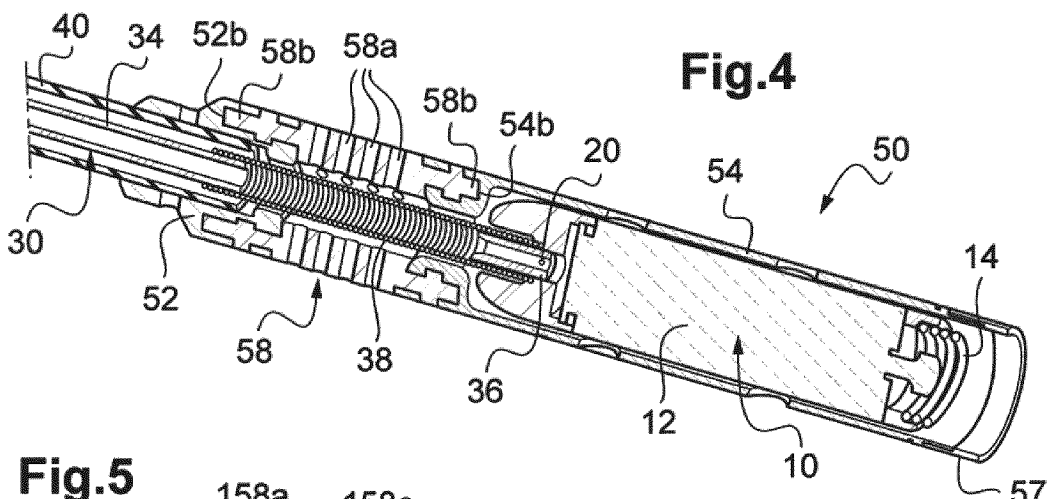
Fig.4
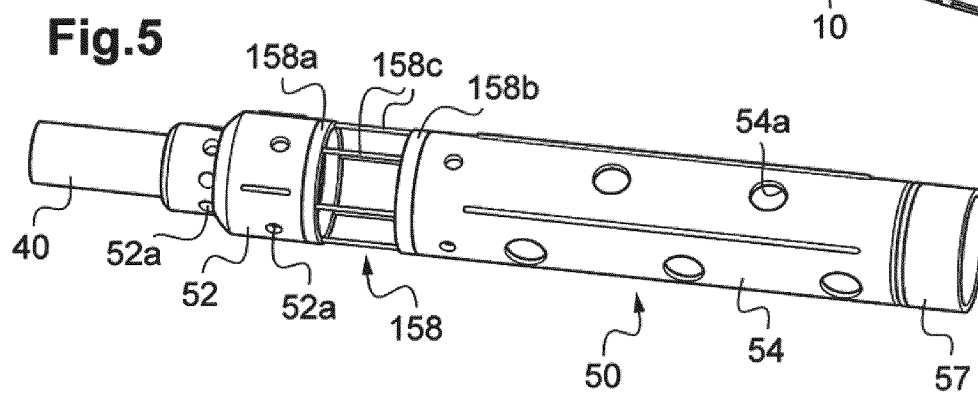
Fig.5
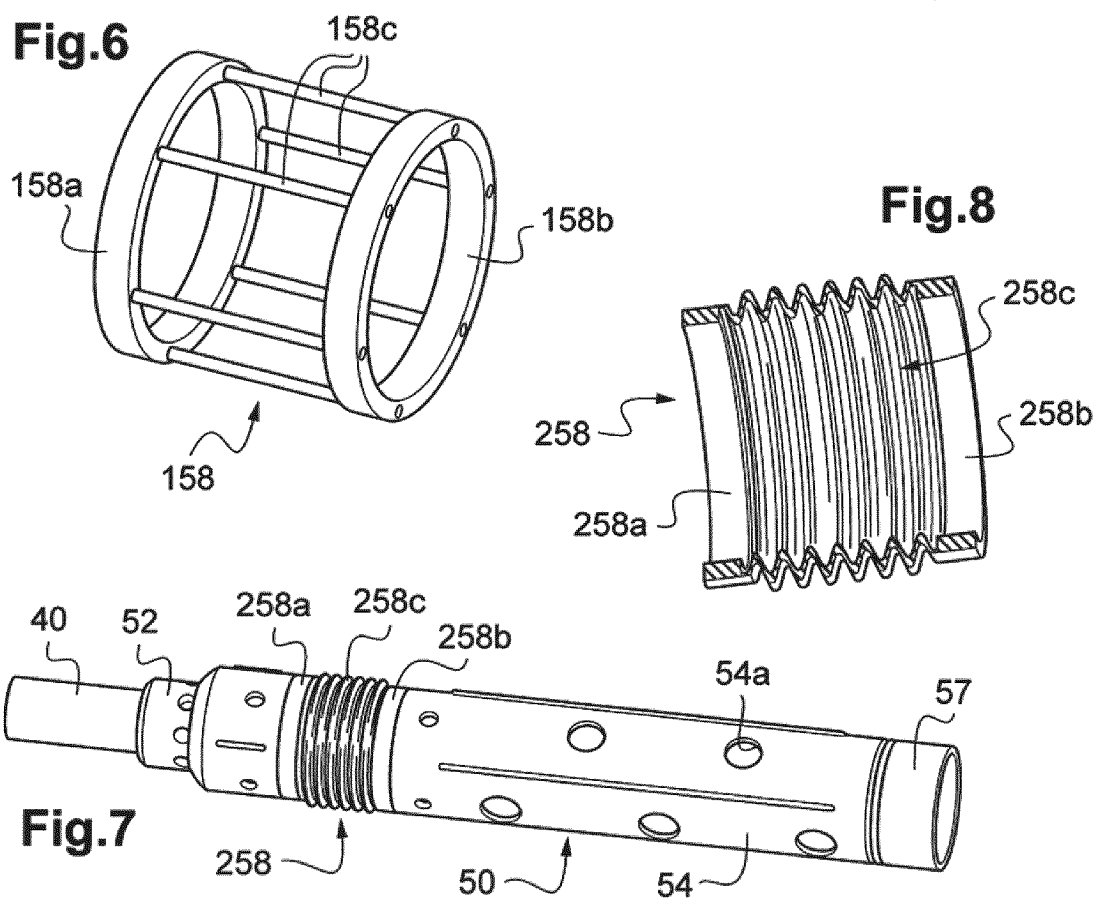
Fig.6
Fig.8
Fig.7

IN SITU IMPLANTATION ACCESSORY FOR AN AUTONOMOUS INTRACARDIAC CAPSULE

CROSS-REFERENCE TO RELATED PATENT APPLICATIONS

This application is a divisional of U.S. patent application Ser. No. 15/071,015 filed Mar. 15, 2016, which claims the benefit of and priority to French Patent Application No. 1552108, filed Mar. 16, 2015, both of which are incorporated herein by reference their entireties.

FIELD

The present disclosure generally relates to "active implantable medical devices" as defined by Directive 90/385/EEC of 20 Jun. 1990 the Council of the European Communities, including implantable devices that continuously monitor heart rhythm and deliver to the heart, if necessary, electrical stimulation, resynchronization and/or defibrillation pulses in the event of rhythm disorder detected by the device.

The present disclosure concerns the in situ implantation of such devices that have at their distal end a device anchoring member adapted to penetrate and anchor to tissue of a body wall at the chosen site of implantation.

BACKGROUND

A non-limiting example of such an anchoring member is a projecting helical screw which axially extends from the body of the medical device and is intended to penetrate and screw into a cardiac tissue at the implantation site. Other non-limiting examples of anchoring members include needles, hooks, barbs, etc. that penetrate the tissue to permanently secure the medical device.

In a particular embodiment, the device is a capsule implanted in a heart chamber (ventricle, atrium or even arterial left cardiac cavity). The capsule may be autonomous, hereinafter referred to as an "autonomous capsule" or "leadless capsule". These autonomous capsules are devoid of any physical connection to an implantable main device (such as the housing of a stimulation pulse generator) or non-implantable device (external peripheral device such as a programmer or a monitoring device for remote monitoring of the patient), and for this reason, they are referred to as "leadless capsules" to distinguish them from electrodes or sensors disposed at the distal end of a conventional lead, which is traversed throughout its length by one or more conductors galvanically connecting the electrode or the sensor to a generator connected to an opposite, proximal end of the lead.

In another particular embodiment, a method is disclosed of delivering or installing, at a chosen implantation site, other types of medical devices, including, for example, stimulation leads in the form of a tubular body having at its distal end an anchoring member for anchoring to a heart wall and an active portion provided with detection/stimulation electrodes, and at its proximal end, mechanical and electrical means for connection to a generator housing, where the generator housing is implanted remotely from the site of application of the pulses. The present disclosure can also be applied to other types of implantable devices, for example, in capsules intended for deliver in situ an active pharmacological agent.

In the case wherein the leadless capsules are endocardial capsules (that is to say capsules to be fixed to the inner wall of a ventricular or atrial cavity, as opposed to epicardial capsules fixed to the external wall of the heart), the implantation constraints are greater due to the approach path, which involves going through the peripheral venous system and then leading under fluoroscopy the capsule to the chosen implantation site, both in an accurate and secure manner. It is only once the site is reached and the capsule is firmly anchored in the heart wall that the operator can "release" the capsule, that is to say, can separate it from the implantation accessory.

EP 2 818 201 A1 (Sorin CRM SAS) describes a system of in situ implantation of an intracardiac capsule with its accessory. The autonomous capsule comprises a cylindrical tubular body provided at its distal end with an anchoring member adapted to penetrate a tissue wall of a cavity of the heart. The remotely steerable implantation accessory comprises a catheter with an internal lumen, extended at its distal end by a protective tubular tip defining an interior volume adapted to receive the capsule, the disconnectable means being provided for supporting and guiding the capsule until the capsule is implanted at an implantation site. The implantation accessory further comprises a sub-catheter movably housed within the lumen of remotely steerable catheter. The sub-catheter and the capsule can be deployed telescopically relative to the catheter between a retracted position wherein the capsule and its anchoring means are completely housed inside the tubular protective tip, and a deployed position wherein the capsule is out to the tubular protective tip and is carried by the distal end of the sub-catheter. Finally, the distal end of the sub-catheter and the proximal region of the capsule are provided with securing means in translation and in mutual rotation, these securing means being disconnectable to drop the capsule once in place.

The EP 2 818 201 A1 document also describes the constraints related to this type of implantation, and the benefits of such a system. The EP 2 818 201 A1 document can be referred to as needed and is hereby incorporated by reference in its entirety.

EP 2394 695 A1 (Sorin CRM SAS) describes a similar implantation accessory but not implementing a telescopic sub-catheter. The capsule is carried by the tip, and coupled thereto by a helical screw system. The implantation is made by bringing into contact the assembly formed by the tip with the capsule inside with the cardiac tissue and anchoring the capsule to the tissue. After anchoring the capsule, a rotational movement imparted to the accessory simultaneously backs the tip and decouples the capsule. As a precaution, a wire or thread connects the tip to the capsule in case it would be necessary to re-intervene to explant the capsule, for example, if the originally chosen site was unsatisfactory after an electrical test, and another site must be found. The wire or thread then guides the tip until it reaches the capsule on which it may then be coupled again to allow explanation of the capsule. The EP 2394 695 A1 document is hereby incorporated by reference in its entirety.

Although this type of device is generally satisfactory, its endovenous and endocardial handling may present some risks because of its size, its form factor, the effort required to transfer power, etc. These risks may include: alteration of venous and/or cardiac tissue, alteration of the tricuspid valve or even cardiac perforation. Indeed, the thickness of the heart wall in close proximity to the classical target (the apex) is of the order of 1 to 2 mm only, and according to the methods of implantation, the doctor may need to directly touch this thin wall with the protective tip itself, operated remotely (by femoral approach) via a powerful remotely steerable catheter, with the transmission of torque and/or a significant axial push.

In addition, the use of such material is relatively undeveloped, as practitioners are instead accustomed more flexible stimulation or defibrillation leads.

OBJECT AND SUMMARY

The present disclosure proposes a system of the aforementioned type, wherein the stresses applied to the environment and pathway during implantation of such a capsule are significantly reduced, thus also reducing the risk of lesion or of injury during implantation, while also protecting the device with its remotely steerable mechanism.

Another object of the invention is to achieve this without significant changes for the practitioner.

Another object of the invention is to enable the practitioner to visually observe the progression of the assembly, such as the tip and the capsule it protects, so that the practitioner may initiate corrective action if necessary.

The invention thus provides an in situ implantation accessory of an independent intracardiac capsule comprising a cylindrical tubular body provided at its distal end with an anchoring member adapted to penetrate and anchor to a tissue wall of a cavity of the heart.

This implantation accessory comprises: a remotely steerable catheter with an internal lumen, extended at its distal end by a tip comprising a base to which the catheter is connected and a cylindrical portion defining an interior volume adapted to receive the capsule; and a sub-catheter housed within the lumen of the remotely steerable catheter with a degree of freedom in relative translation and one degree of freedom in rotation relative to the remotely steerable catheter.

The sub-catheter and the capsule are telescopically deployable from the catheter between i) a retracted position wherein the capsule and its anchoring member are housed inside the tip, and ii) an extended or deployed position wherein the capsule is output from the tip and is carried by the distal end of the sub-catheter, and the distal end of the sub-catheter and the proximal region of the capsule are provided with fastening disconnectable means (e.g., a remotely detachable connector) in mutual translation and bending.

The tip has, between its base and its cylindrical portion, a flexible portion forming an articulation (e.g., joint, hinge, flexible coupling) provides between the base and the cylindrical portion an elastic deformability in bending and in compression.

According to various exemplary embodiments:
The flexible portion may have the shape of a sleeve of an elastically deformable material, the sleeve traversed by a series of orifices, and/or comprising a bellows-shaped region;
The flexible portion may have the shape of a cage, which may comprise two spaced rings for fixation to the base and to the cylindrical portion, and a plurality of elastically deformable bars connecting the two rings to each other in a generally axial direction;
The outer contour of the flexible portion may generally extend in line with the contours of the cylindrical portion in the axial direction of the tip;
The sub-catheter may have, in line with the flexible portion of the tip, a deformation region adapted to facilitate the elastic deformation of said flexible portion, while preserving the necessary effort for the handling of the capsule during rotations or translations, this deformation region may comprise a tubular member formed by windings of a coil, at the ends of which are the main part of the sub-portion of the sub-catheter and the disconnectable securing means to which the capsule docks (e.g., remotely detachable connector);
The protection tip may comprise, on either side of the flexible portion, radiopaque markers;
The flexible portion may be at least partially radiopaque.

DRAWINGS

Further features, characteristics and advantages of the present disclosure will become apparent to a person of ordinary skill in the art from the following detailed description of preferred embodiments of the present disclosure, made with reference to the drawings annexed, in which like reference characters refer to like elements and in which:

FIG. 4 is a perspective view and in half-section of the tip connected to a catheter which receives a capsule connected to a sub-catheter.

FIG. 5 is a perspective view of a tip (and of the associated end of the catheter) according to a second embodiment of the invention.

FIG. 6 is a perspective view of an articulation element of the tip of FIG. 5.

FIG. 7 is a perspective view of a tip (and of the end of the associated catheter) according to a third embodiment of the invention.

FIG. 8 is a perspective view of an articulation element of the tip of FIG. 7.

DETAILED DESCRIPTION

We will now describe, for example, various embodiments of the present disclosure.

Figure 1:
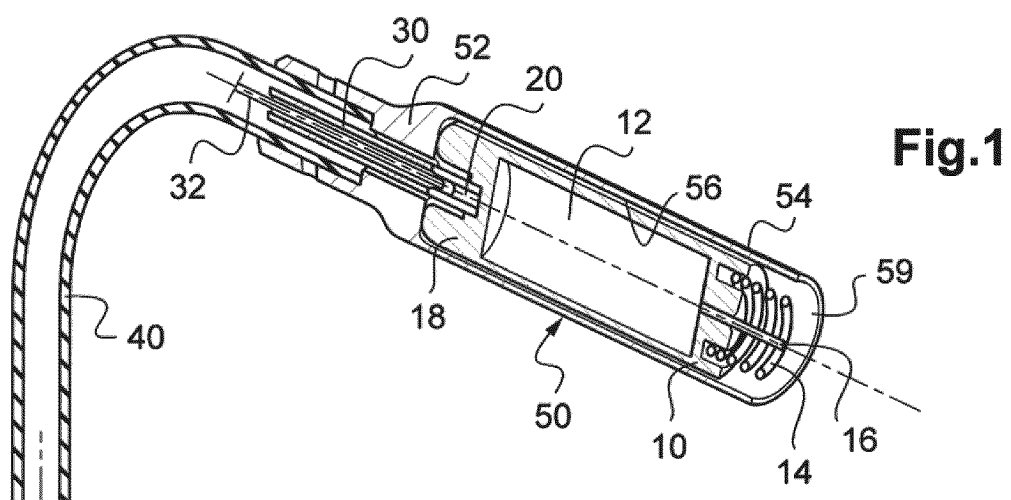
FIG. 1 shows in perspective the general configuration of the various elements of a capsule/catheter/protection tip according to the prior art.

FIG. 1, which illustrates the general architecture of the device, shows an implant accessory of a known type, bearing an autonomous leadless capsule referenced 10.

The leadless capsule 10 comprises a tubular body 12 provided at one of its ends with a projecting helical anchoring screw 14 axially extending the tubular body and integral with the latter in rotation. The anchoring screw 14 comprises in its distal portion a length of the order of 1.5 to 2 mm of non-contiguous turns, adapted to penetrate the heart tissue so as to secure the leadless capsule 10 there. The anchoring screw 14 may be an electrically active screw, that is to say playing, at least at its distal end, the role of a detection/stimulation electrode, or a passive screw only used for anchoring the tubular body 12 in the wall of the heart chamber. In the latter case, the leadless capsule 10 may include a conductive axial needle 16 acting as a detection/stimulation electrode in contact with the myocardial tissue. Alternatively, it is also possible to provide a surface electrode.

The tubular body 12 includes various means and power supply circuits, for signal processing and for wireless communication to enable the exchange of signals with a remote, implantable or not, master device.

At its proximal end 18, the tubular body 12 of the leadless capsule 10 comprises an axial securing rod 20 as described in detail in EP 2 818 201 A1 cited above.

The leadless capsule 10 is intended to be introduced, via the vena cava, from a femoral puncture, as described in the same document.

A remotely steerable catheter 40 is provided at its distal end with a tubular protection tip 50 having a base 52 to which the end of the catheter 40 is fixed and a cylindrical portion 54 defining a central housing 56 for the leadless capsule 10 in a "retracted position" configuration as shown in FIG. 1. The main function of the tubular protection tip 50 is to protect the leadless capsule 10, and in particular the anchoring screw 14, as it moves through the intravenous pathway, with its many curves, angulations, valves, etc. Conversely, the tubular protection tip 50 protects tissues from stripping risks potentially caused by the translational movement of the anchoring screw 14.

According to a particular illustrative embodiment, the outer diameter of the remotely steerable catheter 40 is between 10 and 15 French (6.6 to 10 mm) for an inner lumen diameter of between 8 and 12 French (2.66 to 4 mm). As for the tubular protection tip 50, it must be able to accommodate the leadless capsule 10. Based on the dimensions of a leadless capsule currently manufactured by the Applicant, and according to another particular illustrative embodiment, the inner diameter of the tubular protection tip 50 is about 21 French (7 mm). Various other diameters could be used for the leadless capsule and the tubular protection tip.

According to some embodiments, the catheter 40 may be a reinforced structure, such as a metal mesh or a coil embedded in the thickness of the catheter wall, so as to provide a capacity of torque transmission applied on the proximal maneuver handle to the distal end.

The implantation accessory may include a sub-catheter 30, introduced into the central lumen of the remotely steerable catheter 40, and mobile in rotation and in translation relative to the latter. The sub-catheter 30 may be used to ensure the deployment of the leadless capsule 10 out of the tubular protection tip 50 and to move the leadless capsule 10 to the implantation site by a translational movement over a sufficient length, typically 2 to 6 cm depending on the patient's anatomy.

The sub-catheter 30 may also be used to ensure the transmission of torque from the proximal end (at the operating handle) to the distal end, and may serve as a reinforcement structure.

According to some embodiments the main part of the sub-catheter 30 may be a conventional catheter-guide having a diameter of 4 to 6 French (1.33 to 2 mm), which is an existing, simple and economical device, responding to current torque transmission constraints, with low coefficient of friction inside and outside, with flexibility, etc., and which includes a proximal "Luer-Lock" connection enabling rapid assembly of a multi-function adapter such as a rotational hemostasis valve or of other compatible adapter with this sealed connection standard. Alternatively, the sub-catheter 30 may be used to inject a contrast material to the back of the leadless capsule 10 so as to accurately monitor the operation under image intensification (e.g., fluoroscopy).

The coupling means of the sub-catheter 30 to the leadless capsule 10 at the axial securing rod 20 is of the type described in EP 2 818 201 A1 cited above and will not be described in more detail. Optionally, a retaining wire 32 forming a "breadcrumb" also described in the same document is provided.

Thanks to the coupling means, the release of the capsule may thus be performed as explained in the aforementioned document, by a combined movement of screwing and traction in two steps:
  Screwing of the capsule into the heart wall, by clockwise rotation of the sub-catheter 30, under a slight push, and
  Releasing the capsule, by a further clockwise rotation of the sub-catheter 30, under slight tension in order to permit removal of the sub-catheter.

According to an illustrative embodiment of the present disclosure, a proximal region of the protection tip 50 (proximal side) includes a bendable elastic portion forming a hinge with low rigidity.

Figure 2:
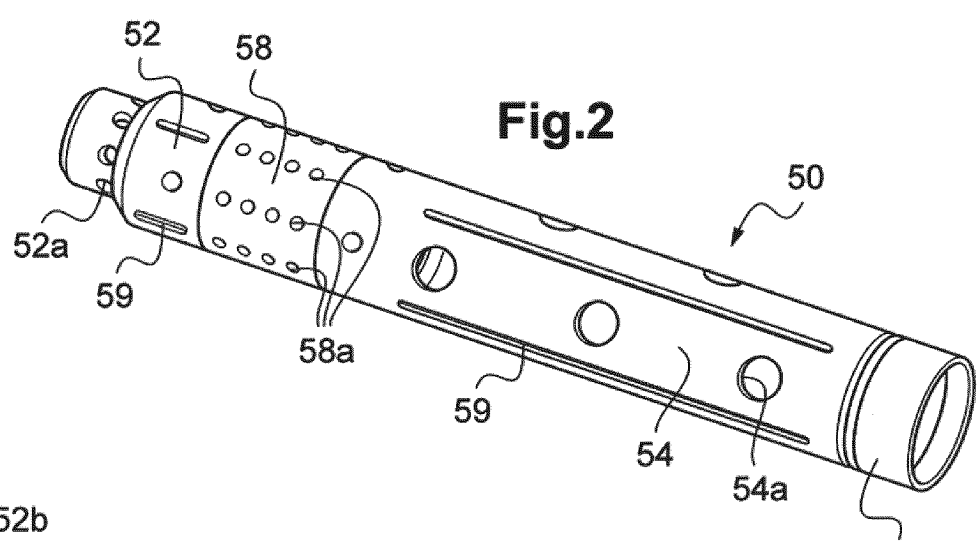
FIG. 2 is a perspective view of a tip according to a first embodiment of the invention.
Figure 3:
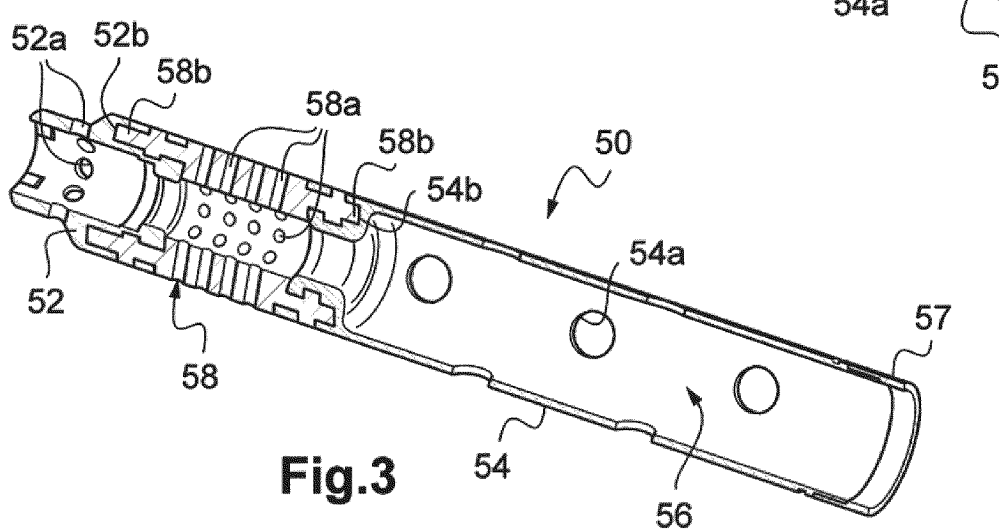
FIG. 3 is a perspective view and in half-section of the tip of FIG. 2.

Referring to FIGS. 2 to 4, according to an illustrative embodiment, a portion of the tubular protection tip 50 includes a sleeve 58 of flexible silicone extending between the base 52 and the rigid protection cylinder 54, in which the sleeve 58 is generally aligned with said protection cylinder 54.

In some embodiments, the sleeve 58 may include one or more openings 58a for decreasing its radial and/or axial stiffness. The shape and arrangement of the openings 58a may vary to ensure the intended function, which may include reducing the axial stiffness of the sleeve and limiting the front contact pressure when the system meets a wall. This particular embodiment also has the advantage of facilitating the flow of blood through the device and of avoiding the formation of clots.

In some embodiments, the base 52 and the protection cylinder 54 may also have holes 52a and 54a, respectively, to facilitate blood flow during implantation.

In some embodiments, the base 52 and the protection cylinder 54 may have longitudinal radiopaque markers 59 not only to allow identification of the positioning of the imaging tip under X-rays, but also to see the play or movement of the flexible joint 58 (e.g., the loss of alignment between the catheter 40 and the tubular protection tip 50, or the mutual approach of these two zones separated by the sleeve 58), thereby allowing the practitioner to relax or adjust the stress if necessary.

The axial ends of the sleeve 58 may be fixed to the rigid elements respectively forming the base 52 and the protection cylinder 54 for example by gluing. As shown in FIGS. 3 and 4, the fixation may be enhanced by an anchor formed by male portions 58b of the sleeve 58 that extend (either locally or over the entire extent of its edges) into the base 52 and the protection cylinder 54 and engage counterpart cavities 52b and 54b, of the base 52 and of the protection cylinder 54, respectively. The male portions 58b and the counterpart cavities 52b and 54b may use shape matching to reinforce the attachment of the sleeve 58 to the base 52 and the protection cylinder 54.

Other attachment means may of course be implemented.

Moreover, in some embodiments, the material forming the sleeve 58 may be loaded with radio-opaque particles so that the behavior of the sleeve 58 may be observed during the procedure.

Alternatively, the sleeve 58 may be made of other flexible biocompatible material such as flexible polyurethane.

It is also possible to provide the distal end region of the protection cylinder 54 with a flexible sleeve 57 made of the same material as the sleeve 58 or of a different material (a technology called soft tip).

In some embodiments, the sub-catheter 30 has, at the level of the sleeve 58, elastic deformation properties including at least one of bending, compression, and rotation. Without such properties, the relaxation provided by the sleeve 58 might be diminished because of the rigidity of the sub-catheter 30. This feature on the catheter can be obtained, in a preferred embodiment and as illustrated by FIG. 4, by providing the structure of the sub-catheter 30, between a main portion 34 and a securing portion 36 with the securing rod 20 for securing of the capsule 10, a connection portion 38 formed by windings of a contiguous or noncontiguous turn of a wire of a material (preferably a metal alloy) with carefully chosen elasticity properties.

As shown in FIG. 4, the main portion 34 and the securing portion 36 of the sub-catheter 30 are inserted into the connection portion 38 and may, for example, be glued.

A description of embodiments of the elastically deformable sleeve 58, in addition to those already discussed, will now be described.

Referring initially to FIGS. 5 and 6, the sleeve 158, is in the form of a cage with two circular rings 158a, 158b interconnected by axially directed peripheral bars 158c. The rings may be made of a rigid material, for example the same as that of the rigid elements 52, 54 of the tip, while the bars 158c can be made for example from a microcable with a diameter of the 0.2 to 0.5 mm made of a biocompatible metal alloy with carefully chosen elasticity properties, such as a nitinol alloy or MP35 NLT. Alternatively, with larger cross-section bars, one can choose to make them into a flexible material such as soft silicone or soft polyurethane.

Such a sleeve has flexibility in bending, compression, and also in rotation.

Furthermore, the wide openings between the bars allow blood flow through the device and limit coagulation.

Another sleeve embodiment is illustrated in FIGS. 7 and 8. The sleeve 258, presents here the general shape of a bellows. More specifically, the sleeve comprises a main zone 258c arranged in the form of a bellows formed in one piece with the end portions in the form of radially thicker rings, respectively 258a, 258b for respectively fastening the sleeve to the base 52 and to the protection cylinder 54 of the tip 50.

Other embodiments of the sleeve are of course possible. For example, it may be formed of a spring with non-contiguous turns of metal alloy. The spring may be covered with a thin layer of silicone to avoid jamming with cardiac or valvular tissue.

It may be advantageous that the outer contours of the flexible portion generally extend in line with the contours of the cylindrical portion in the axial direction of the tip, so as not to impede the progress of the tip housing the capsule as it moves along the access path.

The present disclosure offers numerous benefits, including the following:
  It improves system safety during implantation while requiring no specific action by the practitioner;
  Radiopaque elements or components on the base 52 and on the cylindrical portion 54, and optionally on the sleeve 58, allow fluoroscopic visualization during implantation as an additional safety feature (visual warning to the practitioner);
  The various configurations of the tip do not affect the practitioner's maneuverability of the system through the pathway (e.g. passage through the tricuspid valve);
  The various embodiments do not compromise the smooth and gradual exit of the capsule (no radial or longitudinal locking of the capsule) or its attachment (local elastic deformability of the tip is not likely to interfere with the tip of the screw 14 for anchoring the capsule);
  The system is sterile, has substantially the same footprint as in the prior art, and does not generate significant additional cost for its production;
  Biocompatible materials are readily available to achieve the elastically deformable articulation 58, 158, 258 of the tip.

What is claimed is:

1. A remotely steerable catheter for implantation of an intracardiac capsule comprising:
  a catheter body comprising an inner lumen configured to house a sub-catheter; and
  a tubular protection tip at a distal end of the catheter body, the tubular protection tip comprising:
    a base coupled to the remotely steerable catheter;
    a cylindrical portion defining an inner volume suitable for housing the intracardiac capsule;
    a flexible portion having a first end and a second end, the flexible portion forming an articulation with the first end coupled to the based and the second end coupled to the cylindrical portion, the articulation being able to elastically bend and compress.

2. The remotely steerable catheter of claim 1, wherein the flexible portion is a sleeve of an elastically deformable material.

3. The remotely steerable catheter of claim 2, wherein the sleeve is traversed by a plurality of orifices.

4. The remotely steerable catheter of claim 2, wherein the sleeve comprises a bellows-shaped region.

5. The remotely steerable catheter of claim 4, wherein the bellow-shaped region comprises two end regions having radially thicker rings than a main portion of the bellow-shaped region.

6. The remotely steerable catheter of claim 1, wherein said flexible portion has the shape of a cage.

7. The remotely steerable catheter of claim 6, wherein the cage comprises two spaced rings for fixing to the base and to the cylindrical portion, and a plurality of elastically deformable bars connecting the two rings to each other in a generally axial direction.

8. The remotely steerable catheter of claim 1, wherein the tip comprises radiopaque markers on either side of the flexible portion.

9. The remotely steerable catheter of claim 1, wherein the flexible portion is at least partially radiopaque.

10. The remotely steerable catheter of claim 1, wherein the sub-catheter is moveable in translation and rotation relative to the remotely steerable catheter, a distal end of the sub-catheter extends through a lumen in the base of the tubular protection tip, the distal end of the sub-catheter including a deformation region and a remotely detachable connector for attaching to the intracardiac capsule housed in the tubular protection tip, the deformation region positioned within a lumen of the flexible portion when the sub-catheter and the intracardiac capsule are in a substantially retracted position wherein the intracardiac capsule is substantially disposed within the inner volume of the cylindrical portion of the tubular protection tip.

11. The remotely steerable catheter of claim 10, wherein the deformation region is formed by windings of a coil.

12. A tubular protection tip of a remotely steerable catheter comprising:
  a base configured to couple to the remotely steerable catheter;
  a cylindrical portion defining an inner volume suitable for housing a intracardiac capsule; and
  a flexible portion having a first end and a second end, the flexible portion forming an articulation wherein the first end is coupled to the base and the second end is coupled to the cylindrical portion, the articulation being able to elastically bend and compress.

13. The tubular protection tip of claim 12, wherein the flexible portion is a sleeve of an elastically deformable material.

14. The tubular protection tip of claim 13, wherein the sleeve is traversed by a plurality of orifices.

15. The tubular protection tip of claim 13, wherein the sleeve comprises a bellows-shaped region.

16. The tubular protection tip of claim 12, wherein the flexible portion is a cage.

17. The tubular protection tip of claim 16, wherein the cage comprises:
   two spaced rings for fixing to the base and to the cylindrical portion; and
   a plurality of elastically deformable bars connecting the two rings to each other in a generally axial direction.

18. The tubular protection tip of claim 12, wherein outer contours of the flexible portion extend generally in continuation of the contours of the cylindrical portion.

19. The tubular protection tip of claim 12, wherein the tip comprises radiopaque markers on either side of the flexible portion.

20. The tubular protection tip of claim 12, wherein the flexible portion is at least partially radiopaque.

* * * * *